US010473642B2

(12) United States Patent
Shi et al.

(10) Patent No.: US 10,473,642 B2
(45) Date of Patent: Nov. 12, 2019

(54) EFFECT-DIRECTED IDENTIFICATION OF TARGETED AND NON-TARGETED ANDROGEN DISRUPTORS

(71) Applicant: Nanjing University, Nanjing (CN)

(72) Inventors: Wei Shi, Nanjing (CN); Jing Guo, Nanjing (CN); Hongxia Yu, Nanjing (CN)

(73) Assignee: Nanjing University, Nanjing (CN)

( * ) Notice: Subject to any disclaimer, the term of this patent is extended or adjusted under 35 U.S.C. 154(b) by 200 days.

(21) Appl. No.: 15/261,985

(22) Filed: Sep. 11, 2016

(65) Prior Publication Data

US 2017/0307589 A1 Oct. 26, 2017

(30) Foreign Application Priority Data

Apr. 21, 2016 (CN) .......................... 2016 1 0252354

(51) Int. Cl.
*G01N 33/50* (2006.01)
*G06F 16/245* (2019.01)
*B01D 15/00* (2006.01)
*G01N 33/74* (2006.01)
*C12Q 1/00* (2006.01)
*G06F 19/00* (2018.01)

(52) U.S. Cl.
CPC ......... *G01N 33/5014* (2013.01); *B01D 15/00* (2013.01); *C12Q 1/00* (2013.01); *G01N 33/743* (2013.01); *G06F 16/245* (2019.01); *G06F 19/326* (2013.01)

(58) Field of Classification Search
None
See application file for complete search history.

(56) References Cited

PUBLICATIONS

Brack ("Effect Directed analysis supporting monitoring of aquatic environments—An in-depth overview", Science of the Total Environment, 544 (2016), published on Dec. 1, 2015, 1073-1118) (Year: 2015).*
Durhan ("Methods for Aquatic Toxicity Identification Evaluation", EPA, Duluth MN, 1993) (Year: 1993).*
Blake ("Characterization of the Androgen Sensitive MDA-KB2 cell line for assessing complex environmental Mixtures", Environmental Toxicology and Chemistry, vol. 29, No. 6, 2010, 1367-1376) (Year: 2010).*
Waters ("Beginner's Guide to Size-Exclusion Chromatography", www.waters.com/waters/en_US/Size-exclusion-chromatography-%28SEC%29-Gel-Permeation-Chromatography-%28GPC%29-Guide/nav.htm?cid=10167568&locale=en_US, web capture on Dec. 6, 2018). (Year: 2018).*
Beriro ("Effects of drying and comminution type on the quantification of Polycyclic Aromatic Hydrocarbons (PAH) in a homogenized gasworks soil and the implications for human health risk assessment", Chemosphere 111 (2014), 396-404) (Year: 2014).*
Bjorklund ("Pressurised liquid extraction of persistent organic pollutants in environmental analysis" Trends in Analytical Chemistry, vol. 19, No. 7, 2000, 434-445). (Year: 2000).*
Thomas ("An assessment of in vitro Androgenic Activity and the Identification of Environmental Androgens in United Kingdome Estuaries", Environmental Toxicology and Chemistry, 2002, vol. 21, No. 7, 1456-1461) (Year: 2002).*
Gallampois ("Integrated biological-chemical approach for the isolation and selection of polyaromatic mutagens in surface waters" Analytical, Bioanalytical Chemistry, (2013), 405, 9101-9112) (Year: 2013).*

\* cited by examiner

*Primary Examiner* — Robert J Yamasaki
*Assistant Examiner* — Charles Zoltan Constantine
(74) *Attorney, Agent, or Firm* — Zhihua Han; Wen IP LLC

(57) ABSTRACT

Implementations herein relates to effect-directed identification of targeted and non-targeted androgen disruptors. The implementations include primary separation, androgenic activity testing, high throughput separation and preparation of toxicants, active component scanning based on high performance liquid chromatography-time of flight mass spectrometry, targeted screening of suspicious androgenic substances, non-target identification of androgenic compounds combining mass spectrum, chromatography and toxicity characteristics and toxicity confirmation. The implementations perform separation using SPE and preparative separation in series to obtain high throughput separation fractions, utilize DMSO as a protective agent to optimize concentration of second fractions, utilize target databases to achieve target identification of key toxicants. In addition, assess mass spectrum characteristic identification based on TOF-MS library spectrum, assess chromatography characteristic identification methods based on relationship between retention times and characteristics of compounds, assess toxicity characteristic identification methods based on molecular dynamics simulation techniques, and further assess non-targeted identification and determination of key androgenic substances in the fractions.

6 Claims, 6 Drawing Sheets

EFFECT-DIRECTED IDENTIFICATION OF TARGETED AND NON-TARGETED ANDROGEN DISRUPTORS

CROSS REFERENCE TO RELATED PATENT APPLICATIONS

This application claims priority to Chinese Patent Application No. 201610252354.4, filed on Apr. 21, 2016, entitled "Methods for effect-directed identification of targeted and non-targeted androgen disruptors," which is hereby incorporated by reference in its entirety.

TECHNICAL FIELD

The present disclosure relates to a method for effect-directed identification of androgen disruptors, and more particularly, to a method for toxicity testing based on reporter genes, fractionation of combined environmental samples, androgen disruptors screening, and quantitative and qualitative identification thereof.

BACKGROUND

With continuous economic development, an increasing number of chemicals are released into the environment. There is a wide range of pollutants with complex components, and environmental pollution is often caused by multiple pollutants interacting together. Therefore, chemical analysis methods relying on traditional single-by-discrimination for combined pollution contaminants are difficult to be implemented. Traditional techniques are time and manpower-consuming and may leads to deficient environmental risk assessment. In contrast, new chemical analysis methods such as effect-directed analysis (EDA) combines toxic effects and chemical analysis to effectively identify key toxicants in environmental pollution.

Hormone or endocrine disruptors are compounds that have impacts on endocrine systems of humans and wildlife. Through intake, accumulation and other ways, they play similar roles that natural hormones play in organisms. Even small amounts, they disrupt organisms' endocrine system and cause various anomalies. Therefore, risks of endocrine disruptors in environmental samples deserve attention. At present, researches on endocrine disruptors focus on estrogenic compounds. For androgenic compounds, studies are relatively fewer. Androgenic compounds may interfere at lower concentrations endocrine regulation of normal biological processes and have adverse effects on development and reproductive functions. Currently, a lot of studies have shown that androgenic activity is widely detectable in environmental samples especially in Europe and U. S.

Since a wide variety of contaminants exist in environmental samples, with complex intermediate products and by-products, how to identify main toxic substances in complex environmental samples effectively is extremely important.

It has not been reported that major androgen disruptors may be identified and analyzed by the combination of bioassays, instrumental analysis and toxicity simulation. The proposed disclosure implements androgenic effect-directed identification using solid phase extraction for concentration, preparative chromatography or gel exclusion chromatography sequentially for fractionation, utilizing protective liquid to optimize high throughput fractionation, combining targeted and non-targeted approaches to achieve high resolution mass spectrometry analysis, molecular simulation for toxicant screening, and to enable identification of androgen disruptors in complex environmental samples.

SUMMARY

1. Technical Problem to be Solved by the Present Disclosure

In allusion of growing concern on extraction, separation and screening of key endocrine disruptors in environmental samples with combined pollutions, the present disclosure provides a method for androgenic effect-directed identification of androgen disruptors in combined pollutions of environmental samples. The present disclosure includes (1) molecular weight/hydrophobicity based high throughput separation and reasonable preparation to simplify the complex contaminants in environmental samples; (2) high resolution mass spectrometry qualitative identification, screening and determination combining targeted and non-targeted approaches to approach accurate molecular and constitutional formula; (3) molecular dynamic simulation involved modeling to screen highlighted toxicants. This present may provide a scientific basis for risk assessment of complex environmental pollution.

2. Technical Solutions

To achieve the above object, technical solution provided by the disclosure includes a method for effect-directed identification of targeted and non-targeted androgen disruptors. The method may include the following operations.

(1) Extraction of samples: Solid samples (such as soil, sediment, dust and airborne particulate matter, etc.) are dried, milled and sieved. Accelerated solvent extraction is performed using Dionex ASE350 to extract organic substances. The extraction process first includes three times of extraction using mixed solvent of dichloromethane: N-hexane=1:1 (volume ratio), then extracting using pure methanol solvent three times and collecting separately. Solid phase extraction was performed with amino columns and HLB columns in series for centrifuged or filtered liquid samples (such as surface water and groundwater, etc.) to get more contaminants with different hydrophobicity.

(2) Cleaning up and enrichment: The solid phase extraction columns are activated using 10 mL n-hexane, 10 mL of dichloromethane, and 10 mL of methanol. Extracts of solid samples achieved in step (2) is cleaned up and enriched using amino columns and HLB columns in series, and flow is controlled at 1-2 drops/sec.

(3) Eluting and concentrating: amino columns are eluted using acetonitrile: Toluene=3:1 (by volume); HLB columns are eluted successively with 10 mL of mixed solvents including methanol: Dichloromethane=1:1 (volume ratio), 10 mL of mixed solvents including dichloromethane: N-hexane=4:1 (volume ratio), and 10 mL of hexane. Depending on the eluent, the organic substances are separated into different primary fractions. After rotary evaporation and nitrogen blowing, the eluents are concentrated and diluted to constant volumes in sample vials.

(4) MDA-Kb2 (human breast cancer cells) reporter gene testing: Concentrates of the primary fractions are solvent-replaced by dimethyl sulfoxide (DMSO), and are further diluted to seven different gradients with three parallels. Reporter gene testing using MDA-Kb2 cell is used to detect androgenic and/or anti-androgenic activity.

(5) High throughput separation and preparation: Preparation and separation are performed using preparative chromatography or gel exclusion chromatography for the primary fractions with detectable toxicity. Preparative chromatography techniques are used to effectively perform high-throughput separation of the primary fractions based on hydrophobicity and retention time of fractions. The parameters are provided as follows: preparation chromatograph: Waters AutoPurification HPLC; column: waters preparative column Waters XBridge C18 preparative columns, preparative column dimensions of 19 mm×150 mm, a particle diameter of 5 pm, a flow rate: 5 mL/min; mobile phases: methanol, water; and collection methods: 15 mL of glasses are used to collect according to the time period.

Mobile Phase Gradient:

| Time (min) | Methanol percentage (%) | Water percentage (%) |
|---|---|---|
| 0 | 50 | 50 |
| 50 | 100 | 0 |
| 65 | 100 | 0 |

Gel exclusion chromatography techniques are used to effectively perform separation of the primary fractions based on molecular hydrodynamic volume sizes of compounds. The parameters are provided as follows: Gel exclusion chromatography: J2 Scientific, AccuPrep MPS; materials of column packing: Bio-Beads S-X3; an inside diameter of: 3 cm; a length: 20 cm; eluent: cyclohexane and ethyl acetate (V:V=1:1); a flow rate: 5 mL/min. 15 mL of glasses are used to collect according to the time period.

(6) Concentrating method for second fractionations: The fractionations collected from the preparative chromatographic and Gel exclusion chromatography separation were second fractionations. Direct nitrogen blow is performed to concentrate second fractionations. Since the mixed system of water and methanol is not easy to be concentrated, an overall recovery rates after long time nitrogen blow are less than 20% for some volatile contaminants. During the concentration, DMSO was utilized as a protection agent. This effectively increases the recovery rate of the concentration process. As illustrated in FIG. 1, recovery rates of Polycyclic aromatic hydrocarbons (PAHs) and other standard substances after adding the protection agent into second fractions are all between 80%-120% except for anthracene. Specific concentration operations are provided as follows:

| Fraction | Concentration method |
|---|---|
| Fraction Volume ≤5 mL | After adding protective agent DMSO, directly nitrogen blowing and determine volumes. |
| Fraction Volume >5 mL | After adding protective agent DMSO, performing rotary evaporation and determining volumes. |

(7) Reporter gene testing of second fractions using MDA-Kb2 cell line: A portion of the concentrates of the secondary fraction is obtained, diluted into seven gradients with three parallels for further reporter gene testing based on MDA-Kb2 cell to detect proposed anti-androgenic activity. With standard anti-androgen flutamide for comparison, Graphpad Software for fitting, EC50/IC20 of fractions is achieved to calculate TEQ of each fraction.

(8) Qualitative identification of compounds in fractions: Further analysis on anti-androgenic secondary fractions was performed based on high performance liquid chromatography-time of flight mass spectrometry (HPLC-TOF) to obtain accurate relative molecular mass and secondary mass spectrum, by performing comparison through database of the instrument and an online database (e. g., Chemspider) to obtain a list of suspicious compounds. Instrument parameters used in step (8) includes: HPLC: Agilent 1260; column: Agilent C18 column, size of 2.1 mm×150 mm, a particle diameter of 2.5 μm; a column temperature: 30° C.; a mobile phase: Acetonitrile, a volume percentage of 5% acetonitrile in water; a flow rate: 300 μL/min; Mobile phase gradient provided below:

| Time (min) | Percent Water Content (%) | Acetonitrile percentage (%) |
|---|---|---|
| 0 | 100 | 0 |
| 1 | 100 | 0 |
| 15 | 50 | 50 |
| 25 | 0 | 100 |
| 30 | 0 | 100 |
| 30.5 | 100 | 0 |
| 40 | 100 | 0 |

Instrument parameters further include: MS: Triple TOF 5600-AB ACIEX; Ion source: ESI; ionization mode: positive mode and negative mode; MS scan range: 100-2000 m/z; MSMS scan range: 60-1250 m/z; cluster voltage: ±80V; collision voltage: ±35±15 eV.

(9) Targeted screening of suspicious androgenic substances: It has been reported that 21 types of androgenic substances and 124 types of anti-androgenic substances are in databases. The databases contain chemical names, CAS number, EC20, EC50, characteristic ions and Log Kow of typical androgenic and/or anti-androgenic substances (see patents "Methods for rapid Identification of key androgenic or anti-androgen interference poisons in water samples", Chinese Patent Publication No: CN201310539205.2). Databases of suspicious substance lists may further include potential substances around sampling locations. Mass spectral data analysis software PeakView is used, XIC Manager is used to import target substance databases including characteristics ion pairs of androgenic and/or anti-androgenic substances. The method further comprises: setting peak Intensity>1000, signal to noise ratio S/N>10 and isotope Cl, S, P. Extract primary mass spectrum which are consistent with those in target databases. The substance is determined as the target substance or not based on a determination of matching between the secondary mass spectrum corresponding to the extracted peak and the secondary mass spectrum of the target substance that has been reported in literatures and contains at least two characteristics of secondary ions.

(10) Non-targeted screening of suspicious androgenic substances in fractions: The primary spectrum is obtained using PeakView by retrieving accurate m/z of mass peaks via ion extraction window XIC, and the secondary spectrum of the substance is obtained using Information Dependent Acquisition (IDA), based on information obtained by mass spectrometry, by 7 rules namely by limiting types of elements, valence of restricted substances, unsaturation, and other basic chemical information to obtain molecular formulas; obtaining the secondary spectrum of the substance using Information Dependent Acquisition, obtaining a list of suspicious compounds by comparing chemical compounds from Chemspider and the primary and secondary mass spectrum.

Then based on chromatographic characteristics as a relationship between preparative chromatography retention times and polarities of compounds: Log Kow=0.11501tR- 0.21618 ($r^2$=0.9769), forecasting a polarity range of component substances, or based on different pathways in GPC columns in gel exclusion chromatography due to substances with different molecular weights having different blocks. Accordingly, molecular ranges of the component substances are predictable. Screening in the list of suspicious compounds based on polarity ranges or molecular weight ranges corresponding to retention times of individual fractions, matching of characteristic product ions of substances in literatures and the secondary mass spectrum for further determination of the fraction substances to get a list of suspected compounds. Finally, the toxicity profile is determined for screening of non-target androgen disruptors. Chemoffice is used to construct ligands and receptors of the 3D structure, structures of the ligands are optimized. A Surflex-Dock module of Sybyl software is linked to an AR-LBD active site of a small molecule for a test, then Grimaces 4.0 molecular modeling software is used for MD simulations adopting for field processing CHARMM27 protein receptors and ligand molecules. TIP3P based spherical layers of water molecules are added to every composite system. A minimum spacing edge of a solute and solvent is 10 Å. Sodium or chloride ion is added so that the system is in equilibrium charge state. All systems are used a steepest-descent method to optimize energy and then to restrict ligand positions, within 40 picoseconds (PS) time the temperature rises from 0K to 300K, in the condition of one atmosphere and 300K, balancing 1 nanosecond (ns), and molecular dynamics simulations are followed, wherein the electrical interaction is applied with a particle mesh Ewald (PME) method to calculate, Van der Waals cutoff is set to 10 Å, all simulations for 20 ns, a step is set to 2 femtoseconds (fs), saving every 2 ps. Molecular dynamics simulation data obtained are also processed using GROMACS 4.0, monitoring whether H12 relocation is stable within 20 ns. If the H12 relocation is stable within 20 ns, the implementations determine that the substance has an interfering activity of androgen, thus the suspected androgen disruptors were chosen from the list of suspected compounds.

(11) Quantitatively confirmation of toxicants: For the main screened androgen disruptors, the implementations quantify using high performance liquid chromatography tandem mass spectrometry (LC-MSMS) for quantification.

(12) Toxicity Confirmation: To further confirm the toxicants quantitatively, configuring original blank media based on a concentration obtained from the quantitative analysis of the toxicants, diluting in gradient and calculating toxicity contribution of identified toxicants based on their toxic equivalent.

3. Beneficial Effect

The technical implementations provided by the present disclosure, as compared with existing known art, have the following significant results.

(1) The present disclosure provides a fast and accurate method for androgenic effect-directed identification of androgen disruptors in combined pollutions of environmental samples, which effectively reduces complexity of identification. Primary separation using solid phase extraction and preparative liquid chromatography/gel exclusion chromatography fractionation are implemented sequentially to separate compounds with different hydrophibicities and molecular weights, which effectively reduce complexity of sample analysis. The implementations utilize DMSO as a protective agent to efficiently remain sample composition by improve recovery rates of volatile compounds. The utilized targeted databases including characteristics ion pairs of the reported androgenic and anti-androgenic substances can achieve targeted identification of key toxicants, which efficiently reduced the workload. In addition, the non-target identification is achieved by high resolution TOF-MS, by narrowing suspicious substance range based on hydrophibicity range or mass weight range predicted by retention time of preparative liquid chromatography/gel exclusion chromatography and by implementing further screening of toxicant using toxicity prediction approach, which reduced the workload and cost of purchasing standards. The combination of target and non-target identification ensures wider range of screening, more filter standards, less suspicious toxicants, less workload and cost.

(2) The present disclosure provides a method for effect-directed identification of targeted and non-targeted androgen disruptors. By combining target and non-target analysis, efficiency and accuracy of the analysis are effectively improved which leads to effectively identification of key androgenic substances in complex environmental samples.

(3) The present disclosure provides a method for effect-directed identification of targeted or non-targeted androgen disruptors. The toxicity prediction based on molecular dynamic simulation ensures high throughput screening of suspicious structures, which efficiently reduces the cost of screening time and standards purchasing.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The detailed description is described with reference to the accompanying FIG.s. In the FIG.s, the left-most digit(s) of a reference number identifies the FIG. in which the reference number first appears. The same reference numbers in different FIG.s indicate similar or identical items.

DETAILED DESCRIPTION

To further understand the present disclosure, the accompanying drawings and the implementations of the present disclosure will be described in detail.

The implementations relate to effect-directed identification of targeted and non-targeted androgen disruptors. The implementations may include the following operations.

(1) Extraction of samples: Organic substances in solid samples were extracted following accelerated solvent extraction using Dionex ASE350. The extraction process includes extraction using mixed solvents of dichloromethane and n-hexane (1:1, v:v) for three times and extraction using pure methanol solvents for three times, collected separately.

(2) Solid Phase Extraction: The solid phase extraction columns are activated using 10 mL hexane, 10 mL of dichloromethane, and 10 mL of methanol, extracts from accelerated solvent extraction are further enriched and purified using solid phase extraction columns, and flow is controlled at 1-2 drops/sec.

(3) Eluting and concentrating: sequentially using 10 mL of mixed solution including methanol: Dichloromethane=1:1 (volume ratio), 10 mL of mixed solvents including dichloromethane: N-hexane=4:1 (volume ratio), and 10 mL of hexane to elute substances form the HLB columns for collection. After rotary evaporation and nitrogen blowing, eluent was concentrated in sample vials and volumes were determined. Depending on the eluent, extracted organic substances were divided into four fractions, which were named as 0, 1, 2 and 3 based on hydrophibicity varieties.

Figure 1:
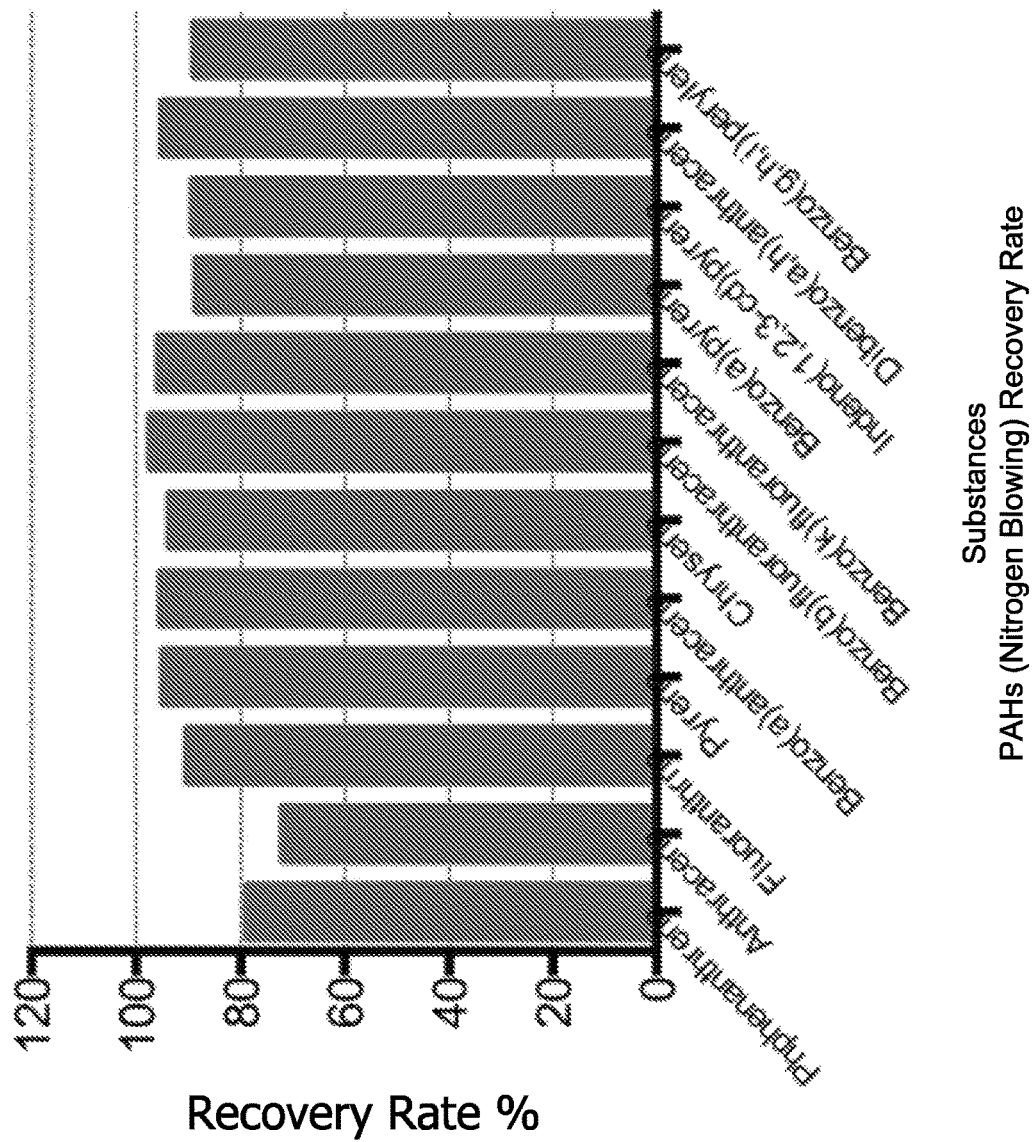
FIG. 1 is a diagram illustrating validation of recovery rates for an optimized method for concentrated preparation of fractions.
Figure 2:
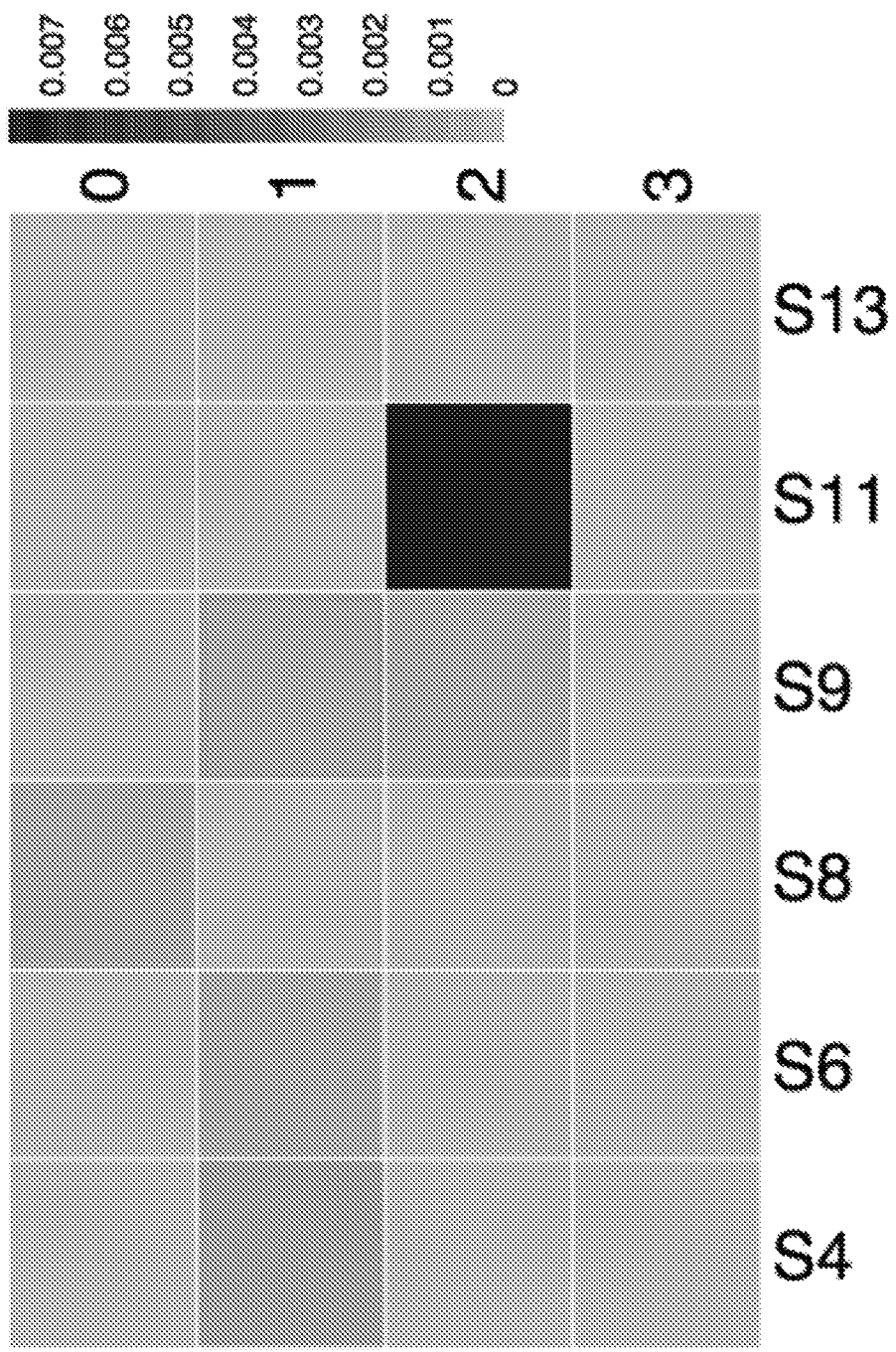
FIG. 2 is a diagram showing toxicity test results of primary fractions separated from sensitive areas of soil samples of Chemical Industrial Park.

(4) Reporter gene testing using MDA-Kb2 cell line: Concentrates of the primary fractions are solvent-replaced by dimethyl sulfoxide (DMSO), and are further diluted to seven different gradients with three parallels. Reporter gene testing using MDA-Kb2 cell is used to detect androgenic and/or anti-androgenic activity. FIG. 2 is a diagram showing primary toxicity test results of fractions primarily separated.

(5) High throughput separation and preparation: Preparative chromatography techniques are used to effectively perform high-throughput separation of the primary fractions based on polarities and retention times of fractions. Its parameters are as follows: preparation chromatograph: Waters AutoPurification HPLC; column: Waters preparative column Waters XBridge C18 preparative columns, preparative column dimensions of 19 mm×150 mm, a particle diameter of 5 µm, a flow rate: 5 mL/min; a mobile phase: Methanol, water; Collection methods: 15 mL of glasses are used to collect according to the time period.

Mobile phase gradient is provided as follow:

| Time (min) | Methanol percentage (%) | Percent Water Content (%) |
| --- | --- | --- |
| 0 | 50 | 50 |
| 50 | 100 | 0 |
| 65 | 100 | 0 |

Collection methods are provided as follows:

| Fraction | Collection time (min) |
| --- | --- |
| 1 | 0.5 |
| 2 | 1 |
| 3 | 1.5 |
| 4 | 2 |
| 5 | 2.4 |
| 6 | 3 |
| 7 | 3.5 |
| 8 | 4 |
| 9 | 4.5 |
| 10 | 5 |
| 11 | 5.7 |
| 12 | 6.2 |
| 13 | 6.7 |
| 14 | 7.2 |
| 15 | 7.7 |
| 16 | 8.2 |
| 17 | 8.7 |
| 18 | 9.2 |
| 19 | 9.7 |
| 20 | 10.2 |
| 21 | 11.4 |
| 22 | 12.6 |
| 23 | 13 |
| 24 | 14 |
| 25 | 15 |
| 26 | 16 |
| 27 | 17 |
| 28 | 18 |
| 29 | 19 |
| 30 | 20 |
| 31 | 21 |
| 32 | 22 |
| 33 | 23 |
| 34 | 24 |
| 35 | 25 |
| 36 | 26 |
| 37 | 27 |
| 38 | 28 |
| 39 | 29 |
| 40 | 30 |
| 41 | 31 |
| 42 | 32 |
| 43 | 33 |
| 44 | 34 |
| 45 | 36 |
| 46 | 38 |
| 47 | 40 |
| 48 | 42 |
| 49 | 45 |
| 50 | 50 |
| 51 | 65 |

(6) Concentrating method for fractionation: During the concentration, the implementations include DMSO as a protection agent to improve recovery rates. Specifically, optimized concentration method is as follows:

| Secondary Fraction | Concentration method |
| --- | --- |
| 1-44 | After adding protective agent DMSO, directly nitrogen blowing, Volume |
| 45-51 | DMSO was added as protective agent after collecting fractions together that belong to each other, performing rotary evaporation and determining volumes. |

Figure 3:
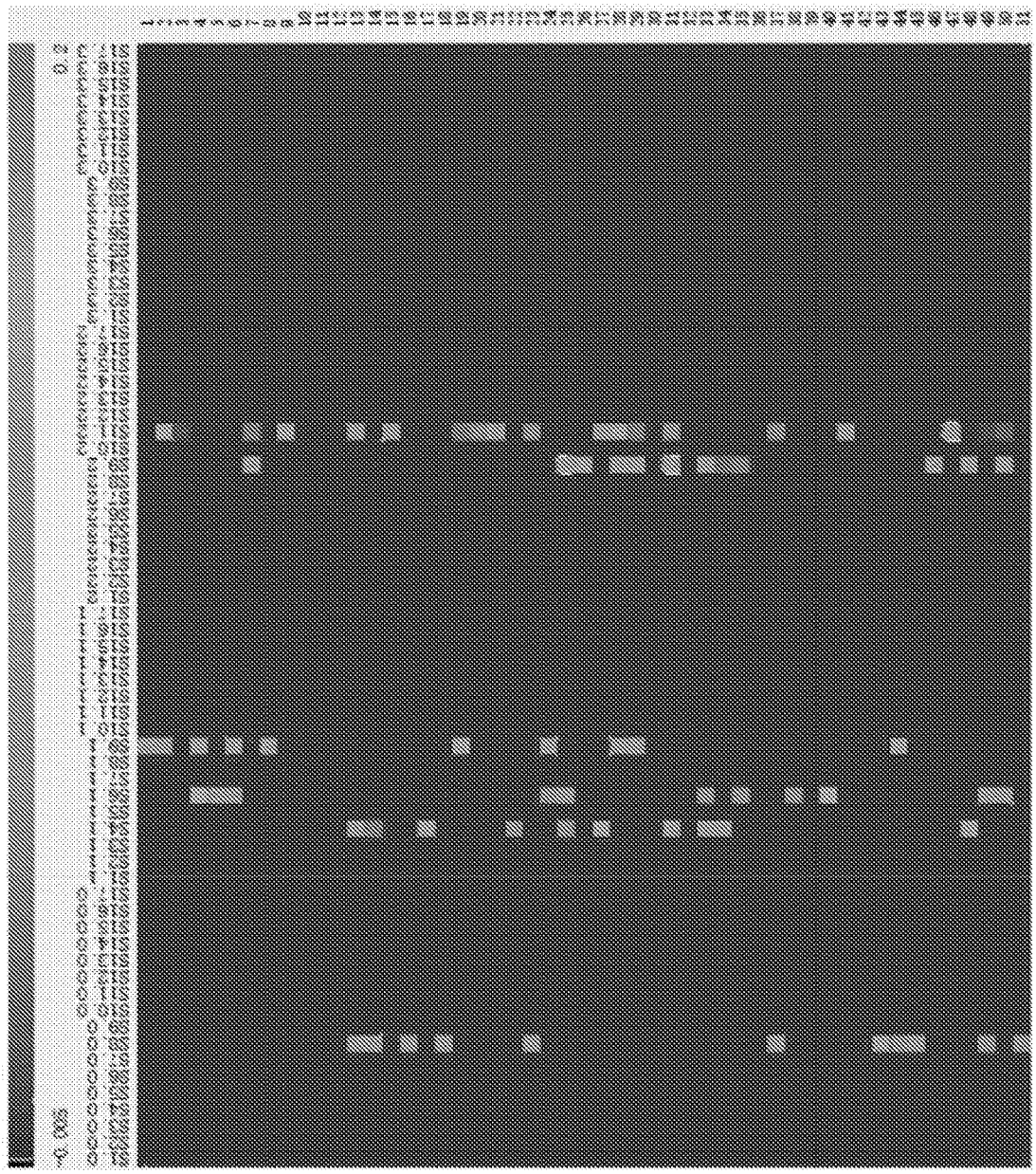
FIG. 3 is a diagram showing toxicity test results of preparative fractions of soil samples.

(7) Separating secondary fractions and reporter gene testing using MDA-Kb2 cell line: A portion of the concentrates of the secondary fraction is obtained, diluted into seven gradients with three parallels for further reporter gene testing based on MDA-Kb2 cell to detect proposed anti-androgenic activity. With standard anti-androgen flutamide for comparison, Graphpad Software for fitting, IC20 of fractions is achieved to calculate TEQ of each fraction. FIG. 3 is a diagram showing toxicity test results from separated fractions prepared using soil sampling points.

(8) Qualitative identification of compounds in secondary fraction 23 of primary fraction 2: Performing further analysis on anti-androgenic secondary fraction 23 based on high performance liquid chromatography-time of flight mass spectrometry (HPLC-TOF), obtaining primary and secondary mass spectrum; and performing comparison through database of the instrument and an online database (e. g., Chemspider) to obtain a list of suspicious compounds. Instrument parameters used in step (8) includes: HPLC: Agilent 1260; column: Agilent C18 column, Size of 2.1 mm×150 mm, a particle diameter of 2.5 μm; a column temperature: 30° C.; a mobile phase: Acetonitrile, a volume percentage of 5% acetonitrile in water; a flow rate: 300 μL/min; and Mobile phase gradient is provided as follow:

| Time (min) | Percent Water Content (%) | Acetonitrile percentage (%) |
|---|---|---|
| 0 | 100 | 0 |
| 1 | 100 | 0 |
| 15 | 50 | 50 |
| 25 | 0 | 100 |
| 30 | 0 | 100 |
| 30.5 | 100 | 0 |
| 40 | 100 | 0 |

MS: Triple TOF 5600-AB ACIEX; Ion source: ESI; Ionization mode: Positive mode and negative mode; MS scan range: 100-2000 m/z; MSMS scan range: 60-1250 m/z; To cluster voltage: ±80V; Collision voltage: ±35±15 eV.

Figure 4:
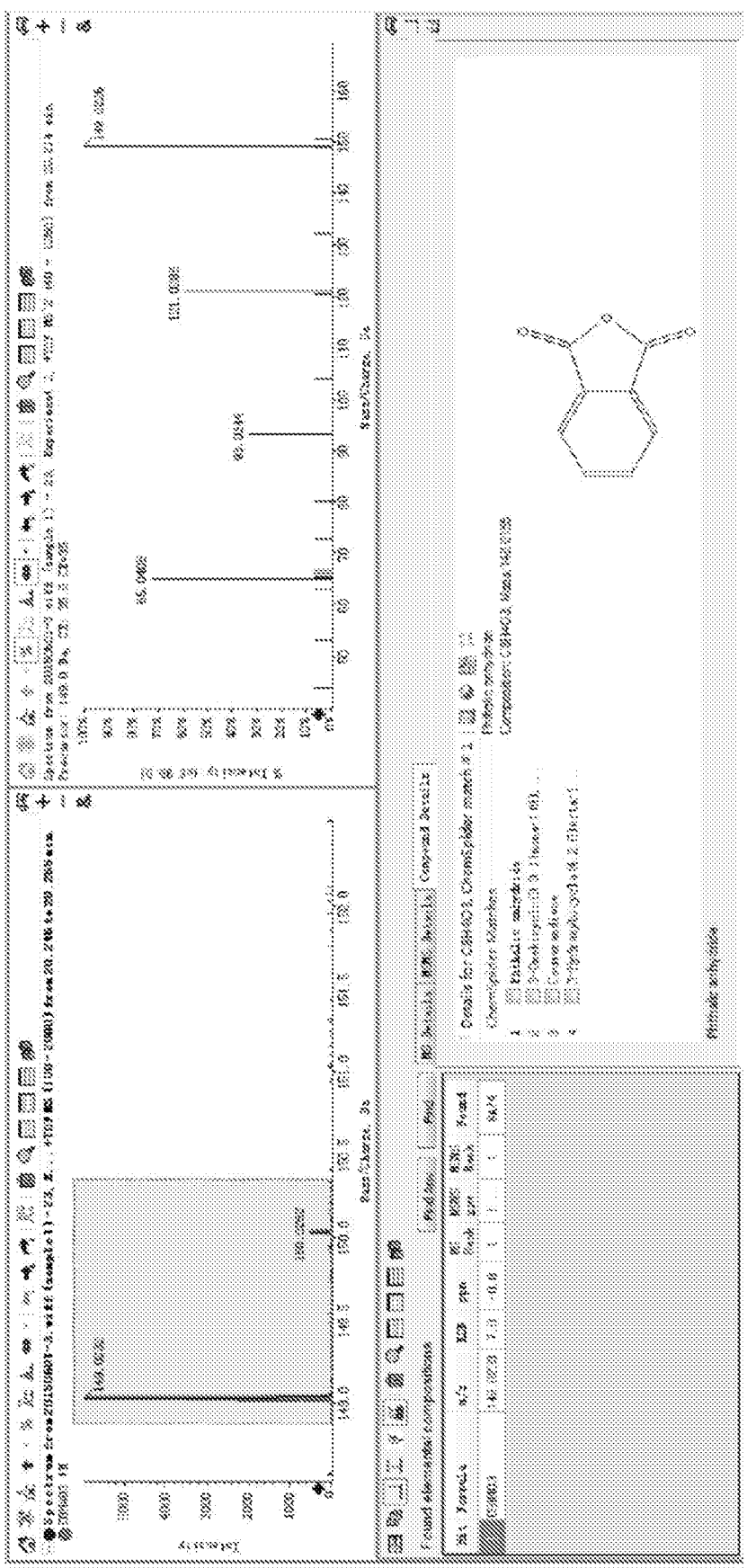
FIG. 4 is a diagram of primary and secondary spectrum showing results of targeted screening of Phthalic anhydride and indicating the presence of phthalic anhydride in the samples.
Figure 5:
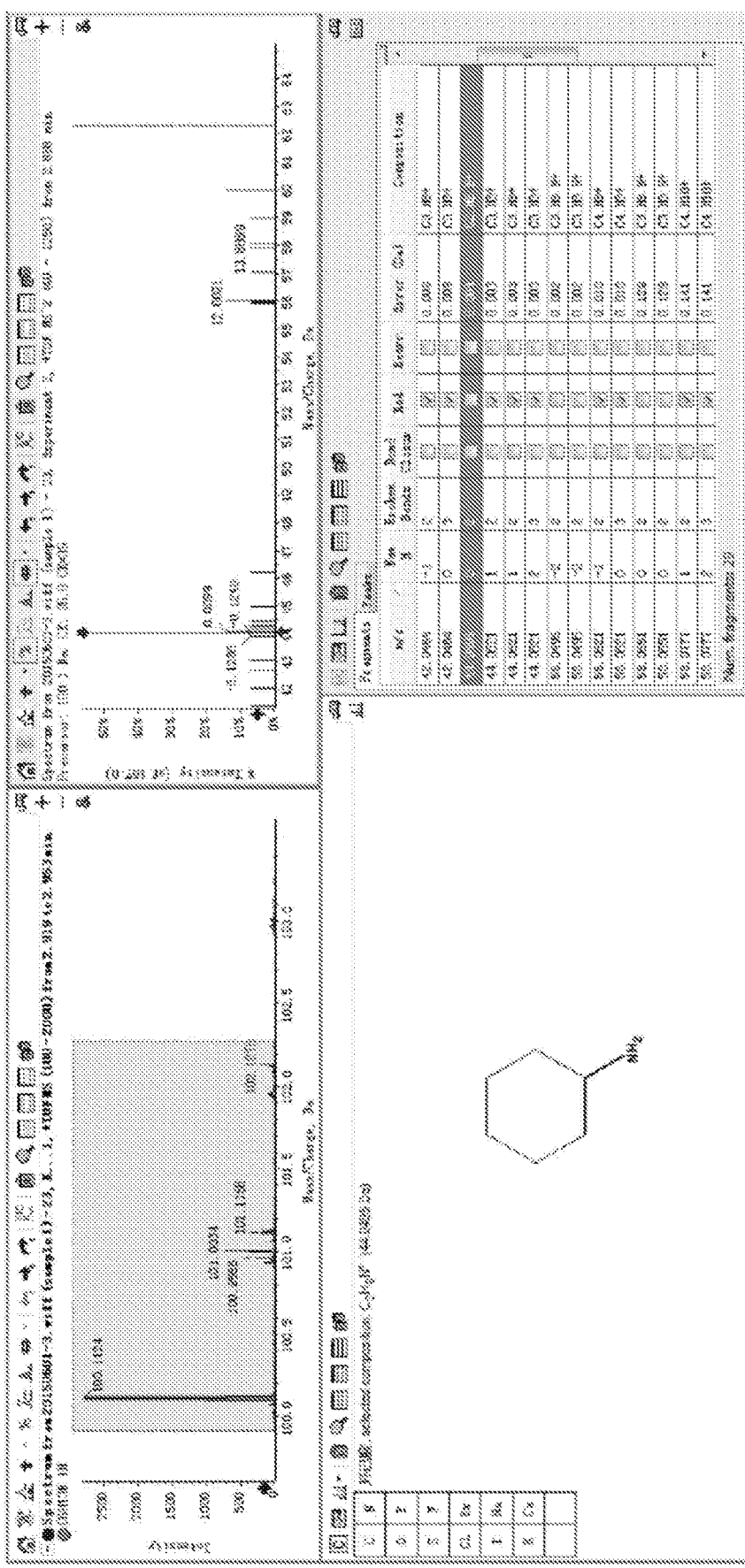
FIG. 5 is a diagram of primary and secondary spectrum showing target screening results of cyclohexylamine and indicating the presence of cyclohexylamine.

(9) Targeted screening of suspicious androgenic substances in secondary fraction 23: It has been reported that 21 types of androgenic substances and 124 types of anti-androgenic substances proposed in databases. The database includes chemical names, CAS number, information related to EC20, EC50, typical characteristic ions, Log Kow associated with androgenic and/or anti-androgenic substances. Further information is also available such as 235 kinds of chemical raw materials and 166 kinds of related chemical products that are registered in Chemical Industrial Park. The registered information includes chemical names, CAS number, information related to EC20, EC50, typical characteristic ions, Log Kow associated with substances registered in Chemical Industrial Park. Mass spectral data analysis software PeakView was used, XIC Manager was used to import target substance databases including characteristics of ion pairs of androgenic and/or anti-androgenic substances and databases including basic physical and chemical information of chemicals registered in Chemical Industry Park. The method further includes: setting peak intensity Intensity>1000, signal to noise ratio S/N>10 and isotope Cl, S, P. Extract primary mass spectrum which are consistent with those in target databases. Followed by literatures or prediction of molecular structure fracture modes, the implementations determines whether the substance is the target substance based on a determination of matching between the secondary mass spectrum corresponding to the extracted peak and the secondary mass spectrum of the target substance that has been reported in literatures and contains at least two characteristics of secondary ions. Targeted screening results are shown in FIG. 4 and FIG. 5.

(10) Non-targeted screening of suspicious androgenic substances in secondary component 23: The primary spectrum is obtained using PeakView by retrieving accurate m/z of mass peaks via ion extraction window XIC, by 7 golden rules Namely by limiting types of elements, valence of restricted substances, unsaturation, and other basic chemical information to obtain molecular formula: C16H35N, obtaining the secondary spectrum of the substance using Information Dependent Acquisition, obtaining a list of 26 suspicious compounds by comparing chemical compounds from Chemspider and the primary and secondary mass spectrum, based on a relationship between preparative chromatography retention time and polarity of compounds: Log Kow=0.11501tR-0.21618, calculating Log Kow ranges of the substance corresponding to secondary component 23:1.16-1.28, screening in the list of suspicious compounds based on hydrophbicity ranges thereof, further screening based on secondary spectrum and those in literatures sharing at least two characteristics of product ions. 4 compounds were screened from 26 possible molecular structures. Screening results are provided as follows:

| category | Chinese name | English name | CAS number |
|---|---|---|---|
| Non-targeted | | DI-SEC-OCTYLAMINE | 5412-92-0 |
| | Hexadecylamine | 1-Hexadecylamine | 143-27-1 |
| | Di-iso-octylamine | Bis(2-ethylhexyl)amine | 106-20-7 |
| | Di-n-octylamine | Dioctylamine | 1120-48-5 |
| targeted | Phthalic anhydride | Phthalic anhydride | 85-44-9 |
| | Cyclohexylamine | Cyclohexylamine | 108-91-8 |

Figure 6:
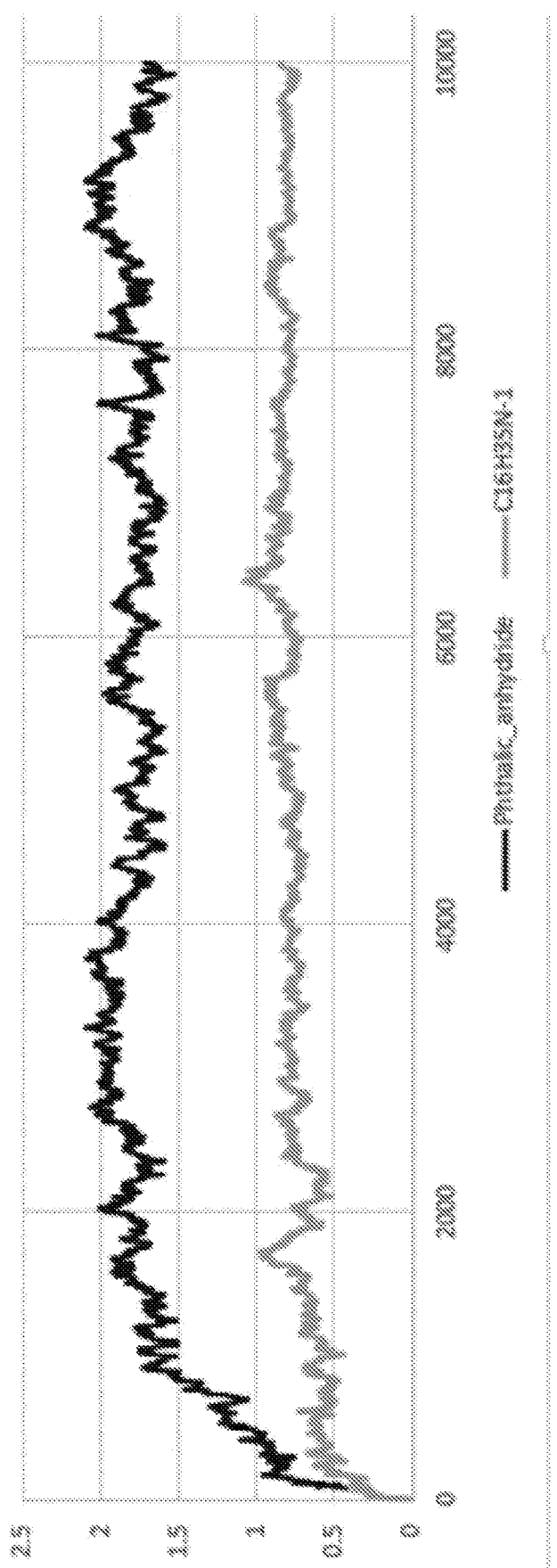
FIG. 6 is a diagram illustrating prediction of anti-androgen toxicity caused by potential toxic structures.

Finally, the toxicity characteristic is determined. Chemoffice is used to construct ligands and receptors of 3D structures, structures of the ligands are optimized, and a Surflex-Dock module of Sybyl software is linked to an AR-LBD active site of a small molecule for a test, and then the implementations use Gromacs4.0 molecular modeling software for MD simulations adopting for field processing CHARMM27 protein receptors and ligand molecules. TIP3P based spherical layers of water molecules are added to every composite system. A minimum spacing edge of a solute and solvent is 10 Å. Sodium or chloride ion is added so that the system is in equilibrium charge state. All systems are used a steepest-descent method to optimize energy, and then to restrict ligand positions, within 40 picoseconds (PS) time the temperature rises from 0K to 300K, in the condition of one atmosphere and 300K, balancing 1 nanosecond (ns) and molecular dynamics simulations are followed, wherein the electrical interaction is applied with a particle mesh Ewald (PME) method to calculate, Van der Waals cutoff is set to 10 Å, all simulations for 20 ns, and a step is set to 2 femtoseconds (fs), saving every 2 ps. Molecular dynamics simulation data obtained are GROMACS4.0 for processing, wherein H12 of phthalic anhydride and di-n-octylamine is stable within 20 ns, determining that the substances are anti-androgenic. The molecular dynamics simulation results are shown in FIG. 6.

(11) Confirmation of toxicants: Standards of identified toxicants were purchased, and high performance liquid chromatography tandem mass spectrometry (LC-MSMS) was used for quantification. Quantitative results are provided as follows, and the implementations further include configuring original blank media based on a concentration obtained from the quantitative analysis of the toxicants, and calculating toxicity contribution of the toxicants.

| | Sampling points | | | | | Possible sources |
|---|---|---|---|---|---|---|
| | S4 | S6 | S8 | S9 | S11 | S13 | |
| Phthalic anhydride (μg/kg soil) | 132 | 114 | 471 | 1158 | 701 | 7 | production material |

-continued

| | Sampling points | | | | | Possible |
| --- | --- | --- | --- | --- | --- | --- |
| | S4 | S6 | S8 | S9 | S11 | S13 | sources |
| Di-n-octylamine (μg/kg soil) | ND | ND | ND | ND | 137 | ND | Amine solvents, intermediates and extraction agent |

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

What is claimed is:

1. An effect-directed method for identification of target androgen disruptors or non-target androgen disruptors, comprising:
   (1) collecting a solid sample or a liquid sample, the solid sample is dried and milled, and the liquid sample is centrifuged or filtered;
   (2) extracting organic substances from the dried and milled solid sample from step (1) using accelerated solvent extraction;
   (3) applying the extracts from step (2) or the centrifuged or filtered liquid sample of step (1) to a solid phase extraction column to enrich potential pollutants, wherein the potential pollutants of different polarities bind to the solid phase extraction column;
   (4) performing primary separation of the enriched potential pollutants by eluting the solid phase extraction column with a series of organic solvents of increasing hydrophobicity to obtain a series of primary fractions;
   (5) testing androgenic or anti-androgenic activity of the primary fractions using a stably transfected MDA-Kb2 cell line;
   (6) performing a high throughput separation and preparation for those primary fractions displaying androgenic or anti-androgenic activity, by generating secondary fractions from those primary fractions displaying androgenic or anti-androgenic activity, wherein the secondary fractions are generated either by preparative chromatography that distinguishes molecular polarity or by gel exclusion chromatography that separates by molecular size, wherein DMSO is added into the secondary fractions as a protective agent during a nitrogen blowing concentrating step within the preparative chromatography procedure in order to achieve a high yield;
   (7) testing androgenic or anti-androgenic activity of the secondary fractions using a stably transfected MDA-Kb2 cell line;
   (8) for the secondary fractions displaying the androgenic or anti-androgenic activity, obtaining a primary and a secondary mass spectrum using high performance liquid chromatography-time of flight mass spectrometry;
   (9) identifying target androgen disruptors through target-screening by steps of: 1) establishing a database comprising molecules associated with androgenic or anti-androgenic activity based on literature search; 2) annotating the molecules in the database with mass spectrum parameters by calculating accurate mass and performing fragment analysis to obtain parameters of potential fragments; and 3) identifying the androgen disruptors by comparing the primary and the secondary mass spectrum with the mass spectrum parameters of the molecules in the database;
   wherein the database comprises molecular formulas, ionization mode and parent mass parameters, and the step further comprises:
   setting peak intensity Intensity>1000, signal to noise ratio S/N>10 and isotope Cl, S, P parameters;
   extracting those primary mass spectrums matching with those in the database;
   wherein a determination of matching comprises a matching of the primary mass spectrum and a matching of the secondary mass spectrum, and wherein the matching of the secondary mass spectrum comprises two or more secondary ions whose characteristics match,
   (10) identifying non-targeted androgen disruptors that do not match the molecules in the database, based on mass characteristics, chromatographic characteristics and toxicity characteristics, wherein the primary and the secondary mass spectrum are used to establish a list of candidate molecules, the chromatographic characteristics are used to predict molecular polarity or sizes, and the toxicity characteristics was predicted from a computer model; and
   (11) purchasing synthetic standards for quantitative analysis and measuring $EC_{50}$ of androgenic activity, calculating toxicity contribution of the androgen disruptors identified in step (9) or (10), extracting and confirming the identified androgen disruptors by configuring blank media based on concentrations obtained from quantitative analysis of the identified androgen disruptors;
   wherein the primary spectrum in step (10) is obtained by retrieving accurate m/z of mass peaks via ion extraction and the method further comprises:
   obtaining the secondary spectrum of the substance using information dependent acquisition,
   obtaining a list of suspicious compounds by comparing chemical compounds from Chemspider and the primary and secondary mass spectrum, and wherein the structures:
     are further filtered based on chromatographic characteristics obtained from relationship between retention times and molecular weight ranges of individual fractions or relationship between retention times and Log Kow of the individual compounds: Log Kow=$0.11501 T_R - 0.21618$, $r^2 = 0.9769$, and
     are further predicted as androgenic or anti-androgenic by using toxicity characteristic, wherein the determination comprises:
   performing molecular dynamics simulation for linkable substances, monitoring whether relocation of H12 of the androgen receptor is stable within 20 ns; and
   determining the substance as suspected toxicants if the H12 relocation is stable within 20 ns.

2. The method of claim 1, wherein the step (2) of extracting organic substances is performed by first extracting twice with a mixed solvent of dichloromethane and n-hexane and pooled, and subsequently extracting twice with a solvent of methanol and pooled, wherein the volume ratio of dichloromethane and n-hexane is 1:1.

3. The method of claim 1, wherein the solid phase extraction column comprises an amino column and a hydrophilic modified styrene polymer column (HLB column) used in tandem, the amino column is eluted with a mixture of acetonitrile and toluene with a volume ratio of 3:1, the HLB column is eluted with 10 mL mixed solvents of methanol and dichloromethane with volume ratio of 1:1, 10 mL mixed solvents of dichloromethane and n-hexane with volume ratio of 4:1, and 10 mL solvent of hexane.

4. The method of claim 1, wherein parameters of the high throughput separation and preparation comprise the following: for gel exclusion chromatography, a column with an inside diameter of 3 cm and a length of 20 cm, an eluent of ethyl acetate and cyclohexane with volume ratio of 1:1, a flow rate of 5 mL/min; for the preparation chromatography, a preparative column with a dimension of 19 mm×150 mm, a particle diameter of 5 μm, a flow rate of 5 mL/min, and a mobile phase of methanol and water.

5. The method of claim 4, wherein the dimethyl sulfoxide (DMSO) in step (6) is added as protection liquid in an amount of 20% of a final volume (v/v) of the secondary fractions prior to nitrogen blowing.

6. The method of claim 1, wherein instrument parameters used in step (8) comprises: HPLC column size is 2.1 mm×150 mm, particle diameter is 2.5 μm, column temperature is 30° C., mobile phase is acetonitrile, flow rate is 300 μL/min, ion source is electrospray ionization, ionization modes are positive ion mode and negative ion mode, MS scan range is 100-2000 m/z, MSMS scan range is 60-1250 m/z, and collision voltage is ±35±15 eV.

* * * * *